United States Patent [19]

Gasparotti

[11] Patent Number: 4,891,386

[45] Date of Patent: Jan. 2, 1990

[54] LIDOCAINE DERIVATIVE AND THERAPEUTIC COMPOSITIONS WHICH CONTAIN IT AS PRINCIPAL ACTIVE INGREDIENT

[75] Inventor: Franca A. Gasparotti, Florence, Italy

[73] Assignee: Molteni & C. Dei F.lli Alitti S.p.A., Florence, Italy

[21] Appl. No.: 651,651

[22] Filed: Sep. 17, 1984

Related U.S. Application Data

[63] Continuation of Ser. No. 291,774, Aug. 10, 1981, abandoned.

[30] Foreign Application Priority Data

Aug. 8, 1980 [IT] Italy .................................. 24104 A/80

[51] Int. Cl.$^4$ ............................................ A61K 31/205
[52] U.S. Cl. ...................................... 514/555; 562/477
[58] Field of Search ................... 260/501.15; 564/194; 424/233; 514/555

[56] References Cited

U.S. PATENT DOCUMENTS 2,382,546 8/1945 Curtis .................................... 424/233
2,441,498 5/1946 Lofgren et al. ...................... 564/194
3,780,081 12/1973 Le Court et al. ............... 260/501.17
4,237,068 12/1980 Boyes et al. .......................... 564/194

OTHER PUBLICATIONS

Nokano, Chem. Abst, vol. 86, #21795d (1977).
Unlisted Drugs, vol. 26, Oct. 1974, No. 10, p. 154.
Chemical Abstracts, vol. 78, Mar. 19, 1973, No. 11, p. 30.

Primary Examiner—James H. Reamer
Attorney, Agent, or Firm—Stevens, Davis, Miller & Mosher

[57] ABSTRACT

A new compound, namely lidocaine salicylate monohydrate of formula:

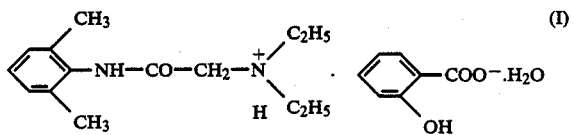

has been proposed, which has shown strong local anesthetic and cardiac antiarrhythmic activity.

4 Claims, 6 Drawing Sheets

LIDOCAINE DERIVATIVE AND THERAPEUTIC COMPOSITIONS WHICH CONTAIN IT AS PRINCIPAL ACTIVE INGREDIENT

This is a continuation of Ser. No. 291,774, filed 8/10/81, now abandoned.

The present invention relates to a new lidocaine salt, the process for its preparation and therapeutic compositions which contain it as their active principle.

More precisely, the present invention relates to lidocaine salicylate monohydrate of formula:

Lidocaine is a compound which has been known for some time as a local anesthetic, and is particularly used clinically for various types of anesthesia by infiltration.

More recently, it has been discovered that lidocaine also has good cardiac antiarrhythmic action, because of which it has been used in cardiology, especially in the immediate treatment of coronary thrombosis.

In reality, when reference is made to lidocaine, it should be noted that lidocaine is always used in the form of one of its salts, in particular the hydrochloride. This is beacuse the instability of the free base, which oxdizes easily in air, and its poor solubility in water, require that a salt comprising a water-soluble anion be used. As the tested salts have all shown the same activity as lidocaine, lidocaine hydrochloride, which is the simplest and most inexpensive salt, is now always used in practice. Lidocaine salicylate monohydrate (I) has now been prepared, and forms the subject matter of the present invention. This is a salt of lidocaine with salicylic acid which, completely unexpectedly, has proved to possess anesthetic and cardiac antiarrhythmic activities that are superior to those of lidocaine both in intensity and duration. The therapeutic index of the new product has also proved significantly greater than that of lidocaine, and no side-effects have followed its administration, because of which the new product can be used in minimum doses and under conditions of maximum safety. Lidocaine salicylate monohydrate is prepared by dissolving equimolecular quantities of lidocaine and salicylic acid in the minimum quantity of water or of an aqueous organic solvent, then evaporating the solution to dryness preferably under reduced pressure, then redissolving the residue in the minimum quantity of a boiling organic solvent, and allowing the crystalline monohydrate salt to separate by cooling.

Ethanol, methanol, acetone or dioxane can conveniently be used as the organic solvent in the first reaction stage; benzene or water can be conveniently used as the solvent in the salt crystallisation stage. In all cases, the organic solvents used must contain 1-2% of water. According to a preferred method of operation, compound (I) is prepared as described in the following example:

750 g (3.2 moles) of basic lidocaine are dissolved in 750 ml of 90% ethanol. 442 g (3.2 moles) of salicylic acid are slowly added under stirring. A clear solution is placed in a rotary evaporator and the solvent is distilled off under vacuum. The mass obtained is redissolved in 2500 ml of boiling benzene, and the solution, filtered if necessary, is left standing.

On cooling, the lidocaine salicylate crystallizes out in the form of transparent crystals having a M.P. of 64°-70°. 1125 g of salt are obtained, equal to 90% of the theoretical. The salt is further crystallized from benzene (100 g in 200 ml). The product obtained in this manner gave the following results on analysis:

M.P. 68°-70° C.

Figure 1:
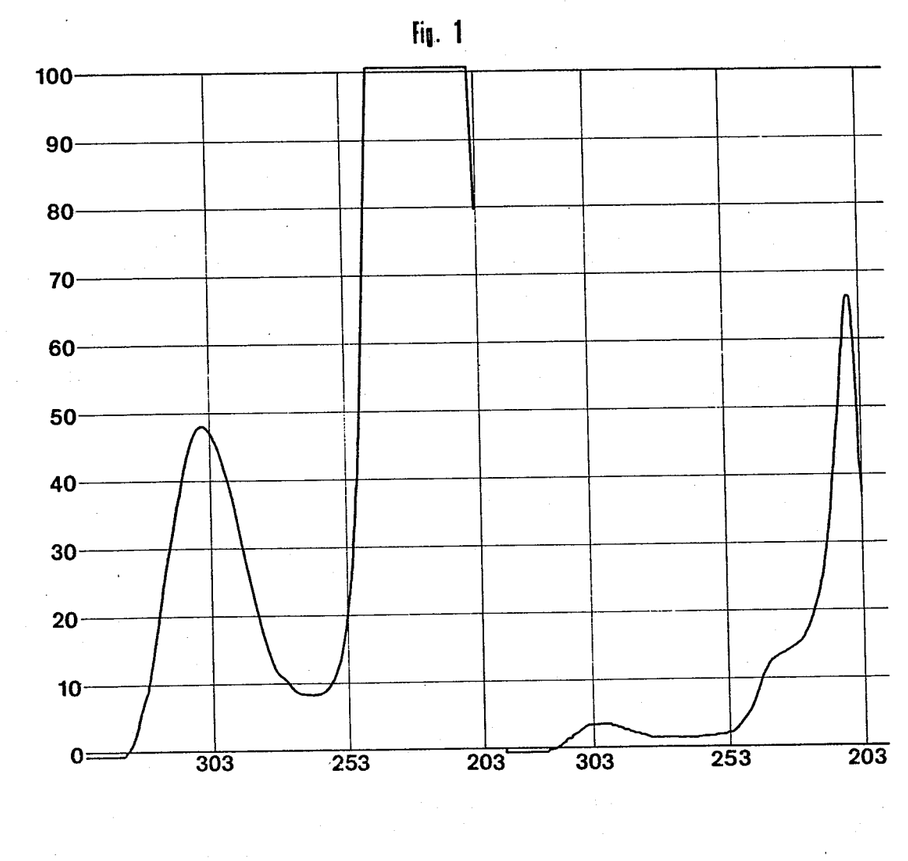
Figure 2:
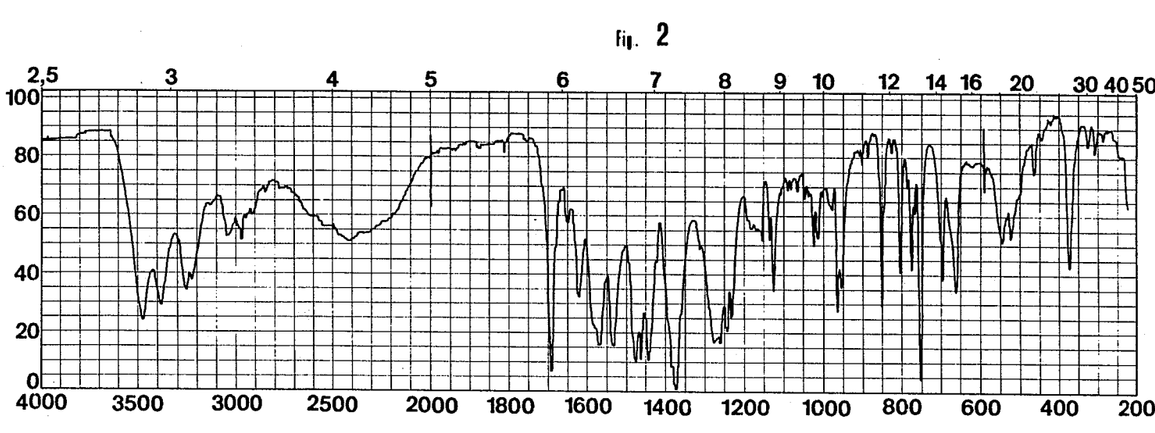

| M.P. 68–70° C. percentage analysis for $C_{21}H_{28}N_2O_4 \cdot H_2O$; M.W. = 390.4 | | | | | | |
|---|---|---|---|---|---|---|
| calculated | N | 7.18 | C | 64.61 | H | 7.69 |
| found | | 7.03 | | 64.68 | | 7.72 | the U.V. spectrum (FIG. 1) shows an absorption maximum at 207 nm (E1%1 cm=1335), a shoulder at about 230 nm and another maximum at 303 nm (E1%1 cm=98)

the I.R. spectrum in KBr (FIG. 2) shows significant bands at 3440 and 3490 cm$^{-1}$, attributed to the phenolic hydroxyl, and a wide absorption at 2300 and 2500 cm$^{-1}$ characteristic of ammonium groups. The bands at 1022 and 1032 cm$^{-1}$, at 962 and 972 cm$^{-1}$, at 860 cm$^{-1}$ and at 385 cm$^{-1}$ are very characteristic. All the aforesaid bands are specific and characteristic for lidocaine salicylate.

Figure 3:
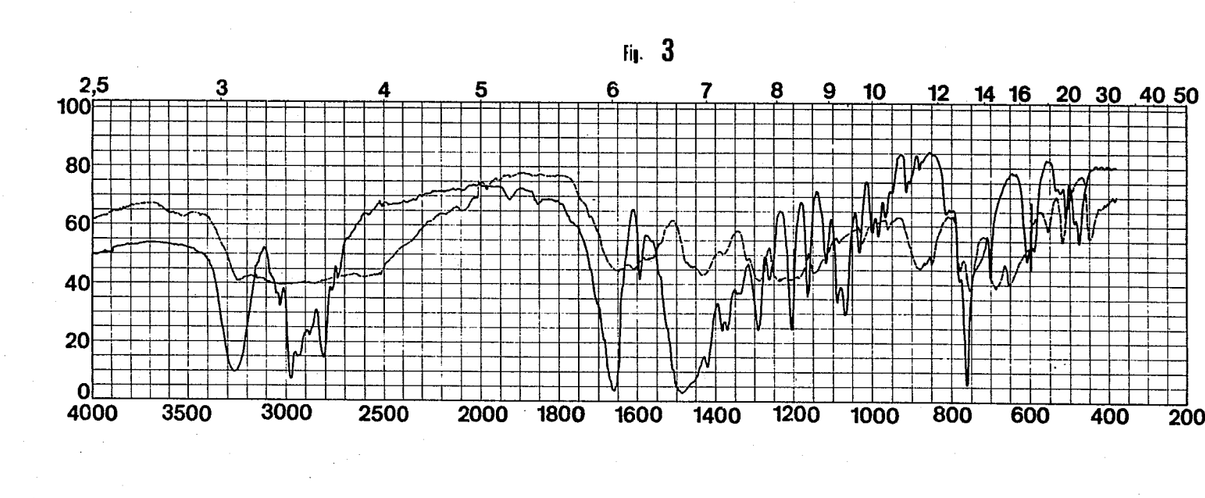

The bands already present in the lidocaine spectrum and in the salicylic acid spectrum are much sharper and more resolved in the case of the lidocaine salicylate, as is clearly apparent by a comparison with the spectra given in FIG. 3 in which graph 1 is the I.R. spectrum of lidocaine and graph 2 the I.R. spectrum of salicylic acid.

the N.M.R. spectrum in DMSO $d_6$ (FIG. 4) shows at low fields a signal at δ9.95 p.p.m., at δ7.7 p.p.m., at δ7.8 p.p.m., at δ7.1 p.p.m., at δ6.8 p.p.m., and at δ6.7 p.p.m. attributable respectively to a NH group, a OH group, a NH+ group, to the three aromatic protons of lidocaine or to the four aromatic protons of the salicylic system.

Figure 4:
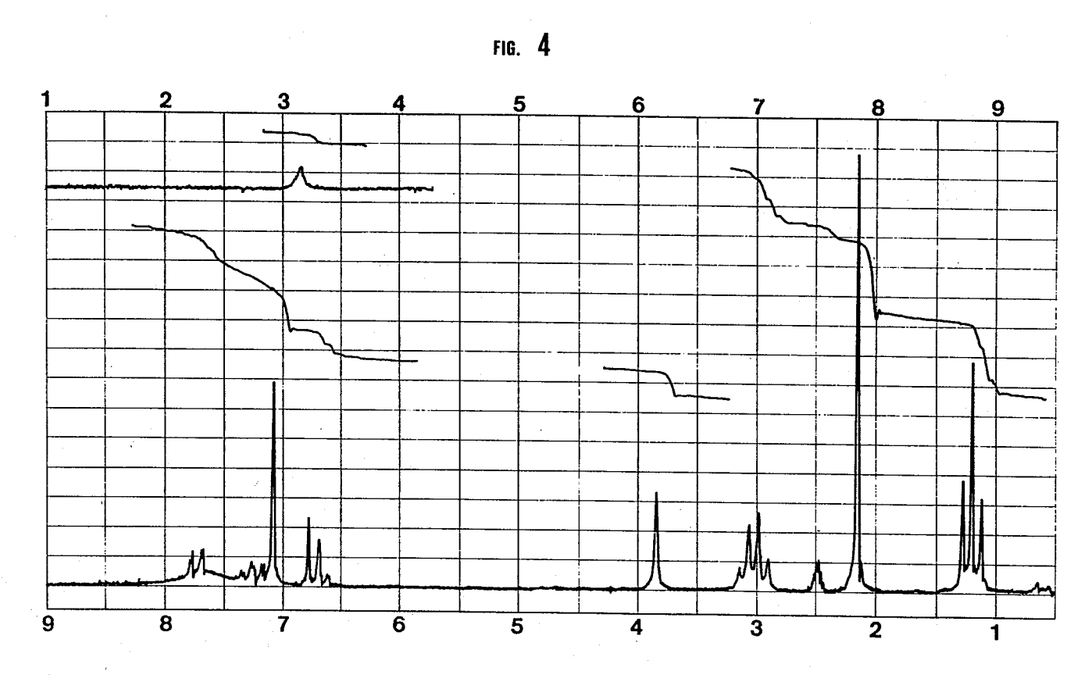

Particularly significant are the values relative to the groups adjacent to the diethylamino group aminoacetic acid which, because of the effect of the salification on the nitrogen, undergo a shift towards lower fields than those of the basic lidocaine. Thus the group attributable to the CH$_2$ of aminoacetic acid is located at δ3.82 p.p.m., in comparison with the δ3.11 p.p.m. of the basic lidocaine, that of the CH$_2$ of the ethyl group is present as a quartet centered at δ3.01 p.p.m. (δ2.61 p.p.m. in the basic lidocaine), and that of the CH$_3$ of the ethyl group as a triplet centered at δ1.2 p.p.m. (δ1.08 p.p.m. in the basic lidocaine). Finally, at 2.12 p.p.m. there is the singlet attributable to the methyl group of the aromatic ring.

As previously stated, the new compound possesses local anesthetic properties which can be demonstrated both by infiltration into the cutis and by apposition on the mucous membranes.

Anesthetic activity by dermic infiltration was determined by the interdermic pompholyx method on the cutis of the back of the guinea-pig in accordance with Bülhring E. and Wajda F. "Biological comparison of local anesthetics", J. Pharmacol. Exp. Ther. 85, 78–84, 1945, by recording the number of negative responses to a set of six suitable stimulations at successive times after administering the drug.

The results obtained are given in Table 1 below, in which each value given is the mean of the determinations in three different animals. Solutions of compound (I) in distilled water were injected.

TABLE 1

Local anesthetic effect by dermic infiltration of lidocaine salicylate into the guinea-pig at a concentration of 0.5%

| Time after administration in minutes | 2 | 5 | 10 | 15 | 30 | 40 | 60 |
|---|---|---|---|---|---|---|---|
| Number of stimulations not followed by a response | 6 | 6 | 6 | 5.6 | 0.3 | 0 | 0 |
| Evaluation of anesthetic effect maximum effect = 100 | 100 | 100 | 100 | 93 | 5 | 0 | 0 |

The same test for evaluating anesthetic activity was repeated in comparison with lidocaine hydrochloride, by injecting equal volumes of 1% solutions of lidocaine hydrochloride and lidocaine salicylate.

The results are given in Table 2 below, in which each value is the mean of the determinations in nine different animals.

Table 2

Comparison between the local anesthetic activity of lidocaine salicylate (L.S.) and that of lidocaine hydrochloride (L.C.) by dermic infiltration into the guinea-pig of equal volumes at a concentration of 1%.

| Time after administration in minutes | | 2 | 5 | 10 | 15 | 30 | 40 | 60 |
|---|---|---|---|---|---|---|---|---|
| Number of stimulations not followed by a response | L.C. | 6 | 6 | 6 | 3.7 | 2.2 | 0.7 | 0 |
| | L.S. | 6 | 6 | 6 | 6 | 2.8 | 2.4 | 1.6 |
| Evaluation of anesthetic effect maximum effect = 100 | L.C. | 100 | 100 | 100 | 62 | 37 | 12 | 0 |
| | L.S. | 100 | 100 | 100 | 100 | 43 | 40 | 17 |

From an analysis of the data given in Table 1 and Table 2 it can be deduced that lidocaine salicylate shows its maximum anesthetic activity even at a concentration of 0.5%. This activity is readily manifested, and is perfectly reversible. In addition, lidocaine salicylate has a local anesthetic activity which is both superior to that of lidocaine hydrochloride and much more prolonged in time.

The local anesthetic effect by apposition on the mucous membranes was evaluated by the corneal anesthesia test in the rat in accordance with Sollman T., J. Pharmacol. Exp. Ther. 11, 1, 1918.

Again, the number of negative responses to a set of six suitable mechanical stimulations at determined times after administration of the drug was recorded.

The results obtained with 0.5% aqueous solutions of lidocaine salicylate are given in Table 3 below, in which each value is the mean of the tests carried out with three different animals.

Table 3

Local anesthetic effect by direct corneal application of lidocaine salicylate in the rabbit at a concentration of 0.5%.

| Time after administration in minutes | 5 | 10 | 15 | 20 | 30 | 45 |
|---|---|---|---|---|---|---|
| Number of stimulatations not followed by a response | 6 | 6 | 5 | 2.5 | 0 | 0 |
| Evaluation of anesthetic effect maximum effect = 100 | 100 | 100 | 83 | 42 | 0 | 0 |

The results obtained with 1% aqueous solutions of lidocaine salicylate and lidocaine hydrochloride applied in equal volumes to the cornea of six different animals (the data given is the mean value of the six tests) are shown in the following table:

Table 4

Comparison between the local anesthetic activity of lidocaine salicylate (L.S.) and that of lidocaine hydrochloride (L.C.) by apposition of equal volumes of 1% solution on to the cornea of the rabbit.

| Time after administration in minutes | | 5 | 10 | 15 | 20 | 30 | 45 |
|---|---|---|---|---|---|---|---|
| Number of stimulations not followed by a response | L.C. | 5.2 | 5 | 1.2 | 0 | 0 | 0 |
| | L.S. | 6 | 6 | 6 | 6 | 2 | 0 |
| Evaluation of anesthetic effect maximum effect = 100 | L.C. | 87 | 83 | 20 | 0 | 0 | 0 |
| | L.S. | 100 | 100 | 100 | 100 | 33 | 0 |

An analysis of the data of Tables 3 and 4 clearly shows that even in local anesthesia by topical application, lidocaine salicylate already produces 100% action at a concentration of 0.5%. A concentration of 1% gives an optimum complete local anesthetic effect for a time of 20 minutes. At the same concentration, lidocaine hydrochloride has only a partial action of very limited duration.

Thus in conclusion, the new compound, lidocaine salicylate, has proved to be a strong local anesthetic both by infiltration into the dermis and by apposition on to the mucous membranes. Its action appears even at very low concentration, is perfectly reversible and is superior to that of lidocaine hydrochloride both in intensity and in duration.

Figure 5:
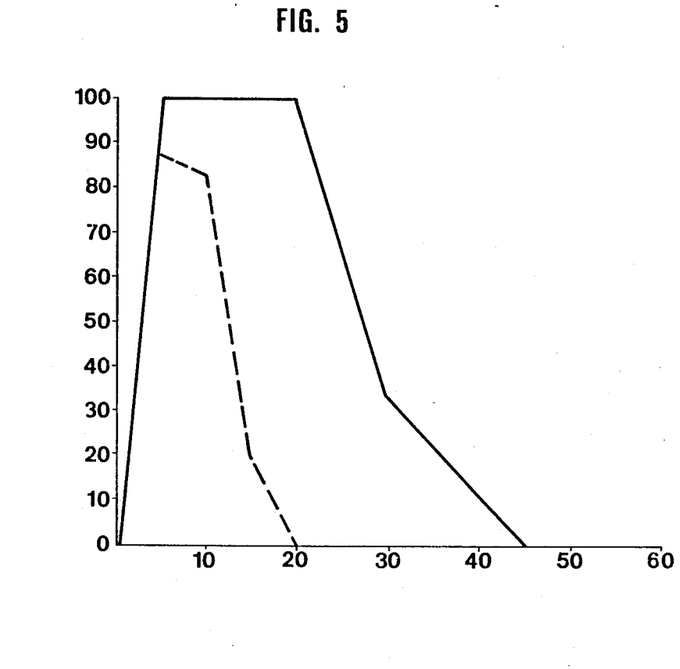

Such a result (which is completely surprising when considering that the salicylate ion is absolutely free in itself of anesthetic activity, and that all other lidocaine salts tested up to the present time have never shown an activity which differs from the basic lidocaine), is very apparent from the graph of FIG. 5 in which the abscissa represents time in minutes, and the ordinate represents the anesthetic effect, total anesthesia being represented by 100.

The dashed curve relates to a 1% solution of lidocaine hydrochloride and the continuous curve relates to a 1% solution of lidocaine salicylate, both applied to the cornea of the rabbit in equal volumes.

The antiarrhythmic (antifibrillatory) activity of the new compound was tested on rabbits by the method of Szekeres L. and Papp. G. Y. J. in "Experimental Cardiac Arrhythmias and Antiarrhythmic Drugs", p. 64–69, 1971, Akedemias Kiedo, Budapest.

According to this method, arrhythmia is induced by slowly injecting (>30 seconds) a 2% aqueous solution of $BaCl_2$ into the marginal vein of the ear in the standard dose of 4 mg/1g of body weight. This dose causes the immediate appearance of rhythm disturbances which remain for more than 30 minutes. The arrhythmia begins with polymorphous extrasystoles of ventricular origin. The cardiac activity is evaluated by electrocardiograph recording.

The tests were carried out by administering compound (I) to 12 rabbits, and lidocaine hydrochloride and sodium salicylate to 12 rabbits in order to allow comparison, and the following results were obtained:

1. Lidocaine salicylate is highly effective in halting fibrillation. The minimum effective dose is 2 mg/kg in a single intravenous administration. An intravenous dose of 3 mg/kg is constantly effective in determining a complete and immediate restoration ad integrum.

The minimum effective dose of lidocaine hydrochloride is 4 mg/kg.

2. The antifibrillatory effect of lidocaine hydrochloride at an intravenous does of 4 mg/kg never lasted beyond 7 min. 30 sec., fluctuating between this maximum value and a minimum value of 2 min. 30 sec. At an intravenous dose of 3–4 mg/kg, lidocaine salicylate controlled the arrhythmia for a minimum time of 14 min. In 25% of the cases, the arrhythmia did not reappear.

3. When injected intravenously in doses of between 1.4 and 3.6 mg/kg, sodium salicylate did not modify the arrhythmia in any way. When injected intravenously subsequently to the sodium salicylate in doses of 4 mg/kg, lidocaine hydrochloride demonstrates the same antifibrillatory activity as demonstrated in animals not previously treated with sodium salicylate. In all the tests carried out, this activity lasted for less than 2 min. 30 sec. This clearly shows that the "in vivo" activity of lidocaine salicylate is not due to the sum of the activities of lidocaine and of the salicylate ion, but is a new action characteristic of the new compound.

Figure 6:
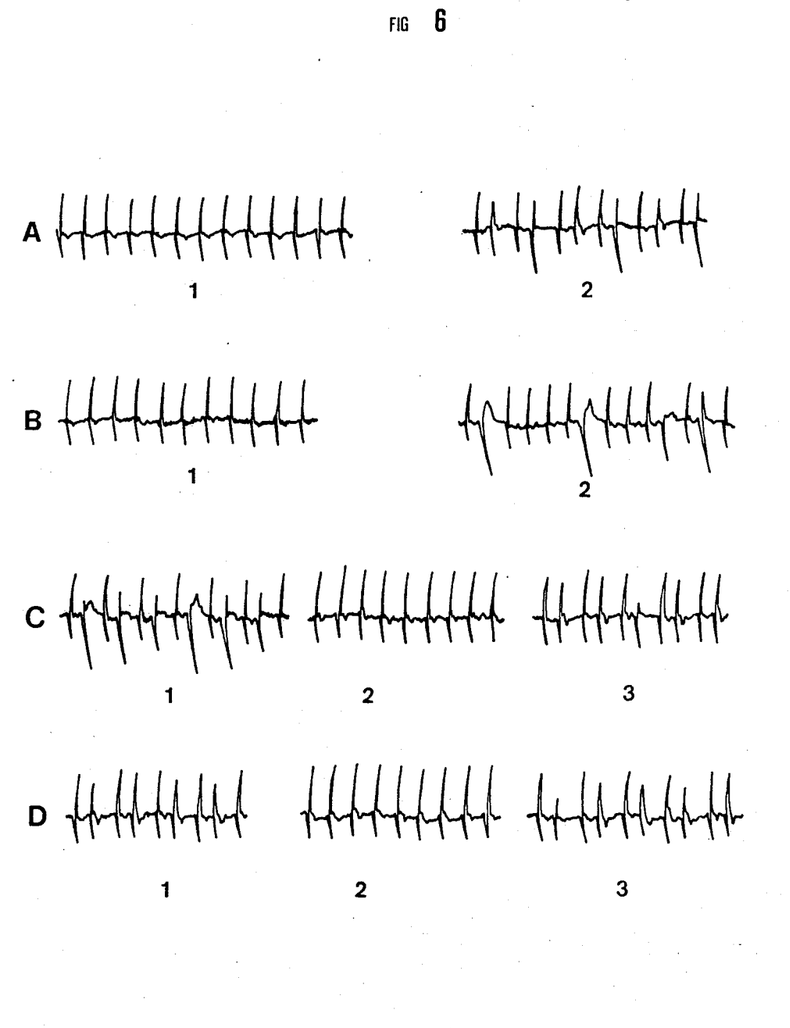

In order to more clearly demonstrate the information stated under the preceding points 1, 2, 3, FIG. 6 shows a significant portion of the prechordial electrocardiogram determined on rabbits under various conditions.

Graph $A_1$ relates to a control; graph $A_2$ relates to a rabbit treated with 4 mg/kg of $BaCl_2$ in which the arrhythmia rapidly appears, to stabilize in a bigeminal pulse rhythm; graph $B_1$ shows the electrocardiogram for the same rabbit returned to normal after administering 4 mg/kg of lidocaine hydrochloride. The electrocardiogram remained as shown in $B_1$ until the seventh minute, after which the arrhythmia reappeared as shown by graph $B_2$. The arrhythmia still exists after 10 min. ($C_1$), treatment with lidocaine salicylate immediately halting the arrhythmia to return to a normal electrocardiogram ($C_2$) for 15 min. After 15 min., the arrhythmia reappears ($C_3$). The arrhythmia is still present after 22 min. ($D_1$) and a further treatment with 4 mg/kg of lidocaine hydrochloride re-establishes normal rhythm ($D_2$). This antiarrhythmic effect lasts only for 4 min., after which the arrhythmia reappears ($D_3$).

In conclusion, it can be deduced that lidocaine salicylate has an immediate antiarrhythmic effect, as has lidocaine, but this effect is produced at about half the dose of this latter, and thus with a much smaller quantity. An extremely important factor is also the fact that the antiarrhythmic effect lasts for at least 15 min., and sometimes completely disappears, in comparison to a maximum duration of action of 7 min. obtained with lidocaine.

The action of lidocaine salicylate was also examined by reference to the cardiodepressing effect. In this respect, it is a known fact that the antiarrhythmic effect is often accompanied in drugs by a cardiodepressing action which makes them dangerous or practically unusable. In the case of lidocaine salicylate, the contractile force was determined on ventricular guinea-pig strips by means of preparations electrically guided at a frequency of 2.5 Hz, and a determination was also made of the refractory period in the atrial function on isolated guinea-pig atria and the ventricular functional refractory period on right ventricular guinea-pig strips (coupled stimulation method of Govier W. C., J. Pharmacol. Exp. Ther., 148, 100–105, 1965) 15 minutes after the introduction of the drug.

The tests were carried out at three different concentrations. Comparison tests under identical conditions were carried out with lidocaine hydrochloride.

The results are given in the following table:

Table 5

"Cardiodepressing" effect of L.S. and L.C. expressed in % of the control values, which are given the value 100.

| Preparation | LIDOCAINE HYDROCHLORIDE | | | LIDOCAINE SALICYLATE | | |
|---|---|---|---|---|---|---|
| | $10^{-6}M$ | $10^{-5}M$ | $10^{-4}M$ | $10^{-6}M$ | $10^{-5}M$ | $10^{-4}M$ |
| Contractile force, ventricular strips from guinea-pig | 93.9 | 93.4 | 50.4 | 100 | 92.7 | 50.9 |
| Beat frequency, isolated guinea-pig atria | 100 | 98.3 | 81.3 | 100 | 97 | 77.8 |
| Refractory period, atrial function isolated guinea-pig atria | 96.1 | 110 | 233 | 89.3 | 105 | 163 |
| Refractory period, ventricular function, right ventricule strips from guinea-pig | 102.6 | 90.7 | 203.2 | 100.7 | 88 | 150 |

From the results of Table 5, it can be deduced that there is no cardiodepressing effect at molar concentrations between $10^{-6}$ and $10^{-5}$.

The cardiodepression becomes apparent at molar concentrations of $10^{-5}$ to $10^{-4}$, i.e. at concentrations of about 10 times greater than those which are reached in the blood on administering 2–4 mg/kg of the drug, i.e. on administering the therapeutic dose of the drug. Thus in terms of the cardiodepressing effect, the new compound (I) has a safety factor greater than 10.

A similar safety margin for the new product was found on determining the acute toxicity.

The $DL_{50}$ for lidocaine salicylate is given in the following table, in comparison with the $DL_{50}$ for lidocaine hydrochloride.

Table 6

Acute toxicity of L.S. and L.C. in the mouse by intravenous administration.

| Compound | No. animals | DL$_{50}$ mg/kg | I.T. |
|---|---|---|---|
| L.C. | 21 | 27 | 6.7 |
| L.S. | 21 | 36.5 | 12.16 |

As can be seen, the toxicity of lidocaine salicylate is, completely unexpectedly, considerably less than that of lidocaine hydrochloride. Moreover, considering that the effective average doses are 4 mg/kg for L.C. and 3 mg/kg for L.S., a much more favourable therapeutic index is obtained for the new compound.

In conclusion, lidocaine salicylate proves completely unexpectedly to be a powerful local anesthetic and cardiac antiarrhythmic agent, the activities of which do not derive from the sum of the inherent activities of lidocaine and of the salicylate ion.

With regard to the antiarrhythmic activity, this is more intense and, in particular, of greater duration than that of the normal lidocaine salts, so allowing a complete and often definitive reversion of a serious ventricular arrhythmia by the intravenous administration of a single dose.

As a local anesthetic, lidocaine salicylate is preferably used clinically diluted with water or fats at a concentration of 0.1-10%.

When used clinically as a cardiac antiarrhythmic agent, lidocaine salicylate is preferably injected intravenously diluted with water in doses of 0.1-10%.

I claim:

1. Lidocaine salicylate monohydrate of formula:

2. Therapeutic compositions containing, as principal active ingredient, therapeutically significant quantities of lidocaine salicylate monohydrate diluted in therapeutically acceptable inert carriers.

3. Therapeutic compositions of local anesthetic action, containing as principal active ingredient therapeutically significant quantities of lidocaine salicylate monohydrate diluted in therapeutically acceptable inert carriers.

4. Therapeutic compositions of cardiac antiarrhythmic action, containing as principal active ingredient therapeutically significant quantities of liodcaine salicylate monohydrate, diluted in therapeutically acceptable inert carriers.

* * * * *